United States Patent
Stanke et al.

(10) Patent No.: US 9,619,878 B2
(45) Date of Patent: Apr. 11, 2017

(54) INSPECTING HIGH-RESOLUTION PHOTOLITHOGRAPHY MASKS

(71) Applicant: KLA-Tencor Corporation, Milpitas, CA (US)

(72) Inventors: Fred Stanke, San Jose, CA (US); Ilya Toytman, Menlo Park, CA (US); David Alles, Los Altos, CA (US); Gregg Anthony Inderhees, Morgan Hill, CA (US); Stanley E. Stokowski, Danville, CA (US); Mehdi Vaez-Iravani, Los Gatos, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 440 days.

(21) Appl. No.: 14/251,312

(22) Filed: Apr. 11, 2014

(65) Prior Publication Data

US 2014/0307943 A1    Oct. 16, 2014

Related U.S. Application Data

(60) Provisional application No. 61/812,248, filed on Apr. 16, 2013.

(51) Int. Cl.
  *G06K 9/00* (2006.01)
  *G06T 7/00* (2017.01)
  *G01N 21/956* (2006.01)

(52) U.S. Cl.
  CPC .......... *G06T 7/001* (2013.01); *G01N 21/956* (2013.01); *G01N 2021/95676* (2013.01);
  (Continued)

(58) Field of Classification Search
  CPC ............ G01N 21/95607; G01N 15/02; G01N 2021/95676; G01N 21/9501; G01N 21/956; G01N 21/95; G01N 21/1717; G03F 1/84; G03F 7/7065; G03F 7/70666; G03F 1/24; G03F 1/20; G03F 7/2039; G03F 1/144; G03F 7/705; G03F 7/70633; G03F 7/70191; G03F 9/7076; G03F 7/001; G03F 7/70408; G03F 7/70625; G03F 1/14; G03F 1/36; G03F 1/44; G03F 1/70; G03F 7/70425; G03F 7/70516; G03F 7/70525; G03F 7/70591; G03F 9/7088; G03F 1/00; G03F 1/32; G03F 1/82; G01J 3/0216; G01J 3/108; G01J 5/0014; G01J 5/0815; G01J 5/0896; G01J 5/08; G01J 5/0862;
  (Continued)

(56) References Cited

U.S. PATENT DOCUMENTS 5,529,862 A * 6/1996 Randall ............... G03F 1/20
                                              430/308
5,808,312 A * 9/1998 Fukuda ............... G03F 1/24
                                              250/492.2

(Continued)

*Primary Examiner* — Vu Le
*Assistant Examiner* — Aklilu Woldemariam
(74) *Attorney, Agent, or Firm* — Dergosits & Noah LLP (57) ABSTRACT

Optical inspection methods and apparatus for high-resolution photomasks using only a test image. A filter is applied to an image signal received from radiation that is transmitted by or reflected from a photomask having a test image. The filter may be implemented using programmed control to adjust and control filter conditions, illumination conditions, and magnification conditions.

20 Claims, 8 Drawing Sheets (52) U.S. Cl.
CPC ...... *G06K 9/00* (2013.01); *G06T 2207/10056* (2013.01); *G06T 2207/30148* (2013.01)

(58) Field of Classification Search
CPC ......... H01J 2237/31791; H01J 37/3175; Y10S 430/168; G06T 2207/10056; G06T 2207/30148; G06T 7/001; H01L 22/20; H01L 22/34; G03H 2001/0094; G06F 17/5081; G06F 2217/12; Y02P 90/265
USPC ........ 382/144, 145, 260; 356/336, 338, 339, 356/343, 445
See application file for complete search history.

(56) References Cited

U.S. PATENT DOCUMENTS

| | | | |
|---|---|---|---|
| 5,849,440 A * | 12/1998 | Lucas | G03F 1/84 382/144 |
| 6,088,505 A * | 7/2000 | Hobbs | G03F 7/001 385/147 |
| 6,177,998 B1 * | 1/2001 | Svetkoff | G01B 11/026 250/559.23 |
| 6,636,308 B1 | 10/2003 | Tsutsui et al. | |
| 6,879,390 B1 | 4/2005 | Kvamme et al. | |
| 7,486,393 B2 | 2/2009 | Kvamme et al. | |
| 7,995,832 B2 | 8/2011 | Xiong et al. | |
| 8,711,346 B2 | 4/2014 | Stokowski | |
| 2003/0138206 A1 * | 7/2003 | Sheng | G02B 6/02138 385/37 |
| 2004/0179184 A1 * | 9/2004 | Levasier | G03F 9/7003 355/75 |
| 2005/0140986 A1 * | 6/2005 | Butler | G03F 7/70633 356/509 |
| 2005/0210437 A1 * | 9/2005 | Shi | G03F 1/14 716/52 |
| 2006/0019177 A1 * | 1/2006 | Mori | G03F 1/82 430/5 |
| 2006/0121360 A1 * | 6/2006 | Wu | G03F 1/14 430/5 |
| 2006/0181700 A1 * | 8/2006 | Andrews | G01N 21/21 356/237.2 |
| 2006/0221322 A1 * | 10/2006 | Tinnemans | G03F 7/70291 355/69 |
| 2007/0134560 A1 * | 6/2007 | Dirksen | G03F 7/70291 430/5 |
| 2007/0146675 A1 * | 6/2007 | Butler | G03F 7/70725 355/69 |
| 2008/0055577 A1 * | 3/2008 | Smeets | G03F 1/14 355/53 |
| 2008/0279442 A1 * | 11/2008 | Den Boef | G03F 1/84 382/144 |
| 2010/0007863 A1 * | 1/2010 | Jordanoska | G01N 21/47 355/53 |
| 2010/0220932 A1 * | 9/2010 | Zhang | G06K 9/6297 382/209 |
| 2011/0304851 A1 * | 12/2011 | Coene | G01N 21/55 356/445 |
| 2012/0123581 A1 * | 5/2012 | Smilde | G03F 7/70483 700/105 |
| 2012/0206703 A1 * | 8/2012 | Bhattacharyya | G03F 7/70633 355/67 |
| 2013/0215404 A1 * | 8/2013 | Den Boef | G01J 3/4412 355/44 |

* cited by examiner

INSPECTING HIGH-RESOLUTION PHOTOLITHOGRAPHY MASKS

TECHNICAL FIELD

This disclosure relates generally to semiconductor device fabrication using photolithographic masks, and in particular, to the inspection of high-resolution photolithographic masks.

BACKGROUND

The fabrication of semiconductor devices involves processing a substrate, such as a semiconductor wafer, to form various integrated circuit features on the substrate. One of the fundamental steps of any semiconductor fabrication process is photolithography, which is a series of steps for building layers of a three-dimensional circuit structure on the substrate. In each photolithography step, a light sensitive photoresist material is applied to the substrate through a mask, exposed to a light source, developed and then etched to form a portion of the three-dimensional structure.

The patterns formed during lithography directly affect the viability and fidelity of the intended integrated circuit features that are ultimately formed. While particles and defects are undesirable at any stage of the fabrication process, mask defects are particularly problematic since they will affect many different devices. Consequently, any defects formed as a result of lithography, such as the transfer of defects that are present on the mask, are problematic for the integrated circuit manufacturing process. Thus, inspection of masks for defects is an important part of quality control for the manufacturing process.

Fabrication processes typically include an inspection tool for inspecting masks for defects in order to predict whether the projected pattern image will faithfully reproduce the intended design of the device. In general, an inspection tool images a test image and a reference image on the mask and detects defects from processing the images. In many cases, an optical inspection apparatus does a good job of resolving the desired patterns on the mask, and sophisticated detection methods may be employed to separate the desired features of the image from defects that are undesirable.

However, for some lithographic methods, the masks are formed with high-resolution patterns that are not resolved well or perhaps not at all by the optical inspection apparatus, and therefore defect detection can be difficult in these cases. For example, an optical inspector having a numerical aperture ("NA") of 0.75 and an inspection wavelength of 200 nm has a "nominal resolution" of 130 nm for 4× features on the mask, which is equivalent to 35 nm resolution on a wafer. Thus, the inspector has a hard optical cutoff for features having a half-pitch of 19 nm on the wafer. There is current interest in extreme ultraviolet ("EUV") lithography to produce, for example, half-pitch lines at 16 nm, which would be completely invisible to the inspector described above. Further, efforts to produce even finer half-pitch lines with nano-imprint lithograph ("NIL") are underway, for example, down to 6 nm half pitch, which would also be invisible to the inspector mentioned above.

Using conventional methods, at least two images are compared, which requires significant computing power and memory to choose or form the reference, to do subtractions, and to make the images as similar as possible for processing. Also, subtraction of images may result in the noise coming from both images combining to form a total noise component which is larger for the difference than for either of the contributors. Thus, it would be desirable to have alternative methods for inspecting, particularly for high resolution masks.

DETAILED DESCRIPTION

This disclosure describes embodiments of an optical inspection apparatus that are inspecting high-resolution photomasks using optimized optical conditions and without differencing test and reference images.

1. Prior Inspection Methods

Using conventional optical inspection methods, a reference image is formed for each portion of the mask that is being sequentially tested for fidelity, and the reference image is compared to a test image. The optical inspection apparatus can derive reference images in various ways. For example, another portion of the same mask that has the same intended pattern can be chosen as the test portion. If there are multiple identical dice on the mask, the reference may be chosen from a different die. In this case, whether the defect is actually in the test or the reference portion is ambiguous. As is well known in the art, if there are more than two dice on the mask, the inspector can use double arbitration. In the case where circuits are made of repeating cells, as is frequently the case, for example, with memory circuits, the inspection apparatus can use a different cell as the reference to compare to the test cell. Such "cell-to-cell" inspection typically requires that the lateral, one- or two-dimensional cell pitch to be known, in order to facilitate finding the right portion of the mask to use as a reference. In yet another case, the inspection apparatus can read a database of the circuit design for the layer being inspected, use knowledge of its own optical system, and render an expected optical image of the test region as a reference.

When comparing a test image to the reference image, the inspection apparatus can adjust parameters in order to make the test and reference images as similar as possible within certain constraints. For example, the inspection apparatus can be configured to shift one or the other of the test and reference images in order to align them. In another example, the inspection apparatus can equalize the color scales of the images to minimize the difference between them. Finally, the inspection apparatus can detect defects by looking for deviations in the difference between the test and reference images that exceed some threshold level. For a portion of the mask that is defect-free, the difference between test and reference image is expected to be nominally zero, with some noise due to tool issues such as shot noise and speckle in the images, changes in focus between dice or cells, and errors in the rendering of the database design to an optical image. The inspection apparatus can erroneously detect defects if the noise exceeds the detection threshold, and such false detection is obviously highly undesirable.

While typical photolithography methods use a 4:1 optical demagnification of the mask onto the substrate, making the actual structures on the mask quite large, high-resolution methods, such as nano-imprint lithography ("NIL"), uses contact transference of patterns on the mask with a demagnification factor of 1:1. In some cases, for producing the same target structures on the substrate, an optical inspection tool will be able to resolve the pattern on an optical mask but not on the NIL mask.

Figure 1A:
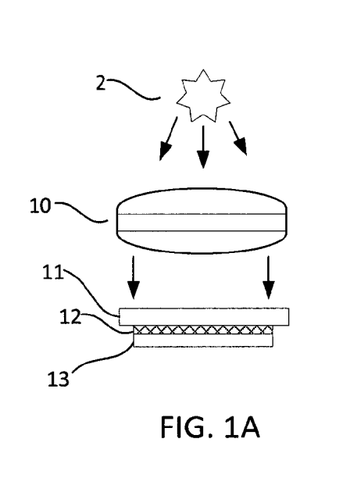
FIG. 1A is a schematic diagram illustrating the contact method of printing patterns from a lithographic mask.
Figure 1B:
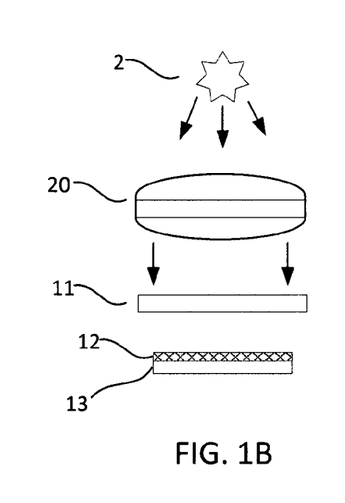
FIG. 1B is a schematic diagram illustrating the proximity method of printing patterns from a lithographic mask.
Figure 1C:
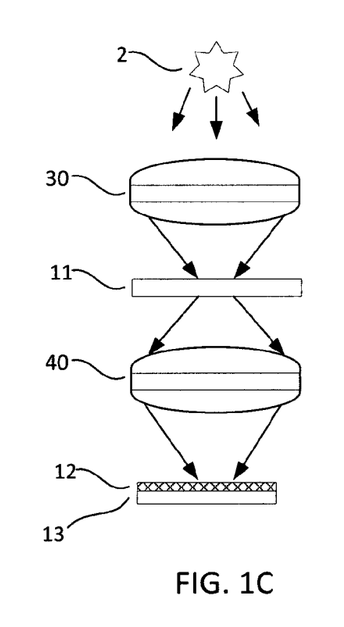
FIG. 1C is a schematic diagram illustrating the projection method of printing patterns from a lithographic mask.

For example, FIG. 1A illustrates the method for contact transference of patterns, where a light beam 2 is directed through illumination optics 10 onto mask 11, which is in direct contact with the photoresist layer 12 on wafer 13. FIG. 1B illustrates the method for proximity printing, where the light beam 2 is directed through illumination optics 20 and onto mask 11, then across a small gap (10 to 25 microns) to the photoresist layer 12 on wafer 13. Finally, FIG. 1C illustrates the method for projection printing, where the light beam 2 is directed through illumination optics 30 onto mask 11, then through magnification optics 40 to the photoresist layer 12 on wafer 13.

One option for inspecting NIL masks is to use a scanning-electron microscope ("SEM"), which produces images by scanning a sample one portion at a time with a focused beam of electrons. However, SEM scanning is generally much slower than optical scanning, which collects the entire image simultaneously. Thus, the loss of useable mask time due to SEM inspection is typically cost prohibitive.

In another case, high-resolution patterns can also be formed using extreme ultraviolet ("EUV") lithography to transfer patterns from an EUV mask to the substrate using radiation having an approximate wavelength of 13.5 nm. At the present time, however, there are no mask inspection tools using EUV that can provide comparable resolution in the same modes as optical inspectors inspecting optical masks. An optical inspector operating at a wavelength of ~193 nm, for example, can be used to inspect EUV masks, but may have little or no resolution of the desired patterns on the masks.

In yet another case, hybrid lithography methods are being developed due to the delay in development of practical EUV lithography. For example, it is possible to produce very fine, one dimensional lines and spaces on a mask in a single lithography step, and then make low resolution cuts in the lines with another step. This method places tight constraints on the device design, which can be expensive to implement, but worthwhile in terms of manufacturability.

Methods for processing test and reference images to determine defects are known, for example, from U.S. Pat. No. 7,564,545 entitled Inspection Method and Systems for Lithographic Masks, which is incorporated by reference in its entirety herein. Methods and apparatus for inspecting lithographic masks are known from U.S. Pat. No. 7,486,393 entitled Multiple Beam Inspection Apparatus and Method, which is incorporated by reference in its entirety herein.

2. Optical Inspection Apparatus

Figure 2:
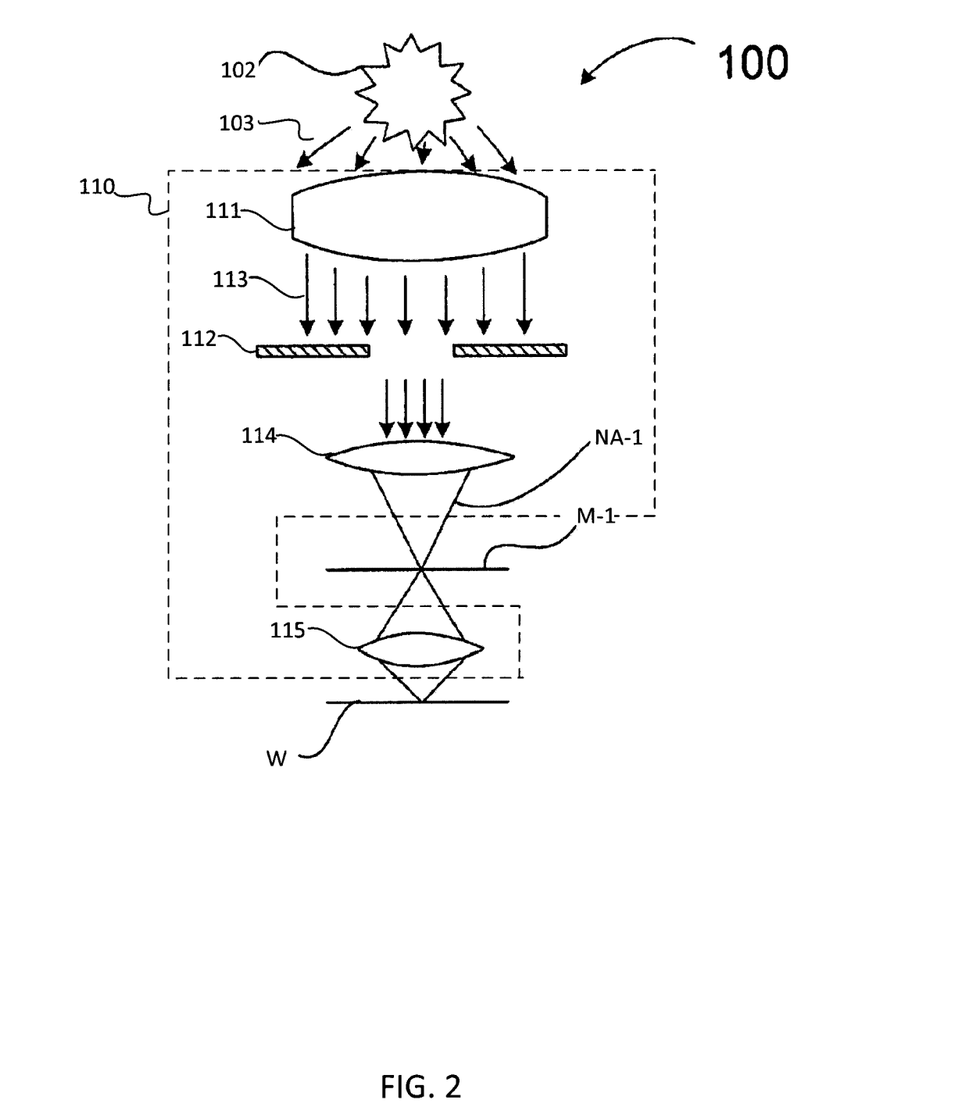
FIG. 2 is a schematic diagram illustrating a tool for printing patterns from a lithographic mask onto a wafer.
Figure 3:
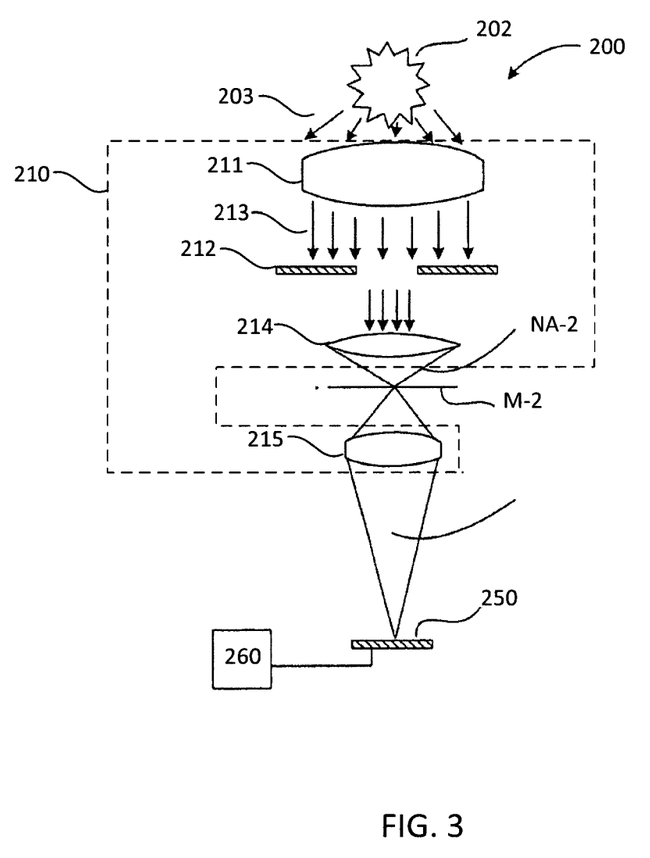
FIG. 3 is a schematic diagram illustrating a tool for inspecting a lithographic mask.

FIG. 2 is a simplified schematic diagram of an apparatus 100 useful for transferring a pattern from a mask M onto a wafer W as part of a semiconductor fabrication process, while FIG. 3 is a simplified schematic diagram of an apparatus 200 useful for inspecting the mask M prior to using the mask in a semiconductor fabrication process.

Referring to FIG. 2, the lithographic pattern transfer apparatus 100 may be implemented as a scanner or stepper, such as the PAS 5500 automatic stepper available from ASML Holding NV. Other similar machines are available from Nikon Corporation, Canon, Inc. and Ultratech, Inc., for example.

In general, an illumination source 102 emits radiation 103 of a desired wavelength through illumination optics 110 onto one or more selected portions of the mask M. In one simplified embodiment, the illumination optics include a first lens arrangement 111 for collimating the light beam 103 into collimated light beam 113; a modulator 112 for restricting the transmission field; a second lens arrangement 114 for focusing the beam 113 that is transmitted through the modulator into one or more illuminations spots having the specified numeric aperture NA-1 at the plane of the mask M; and a third lens arrangement 115 for focusing the radiation that is transmitted through the mask onto the substrate W to create the desired pattern on the substrate.

Modern lithographic transfer and inspection systems are known that provide desired radiation at wavelengths of 248 nm, 193 nm, 157 nm, or extreme ultra violet ("EUV") at 13 nm, or nanoimprint lithography ("NIL") at less than 10 nm resolution, or even electron-beam or particle-beam exposure.

Referring to FIG. 3, one embodiment of the inspection apparatus 200 has an optics system 210 similar to that of FIG. 1, with first lens 211, collimated beam 213, modulator 212, second lens 214, and third lens 215. However, in this embodiment, lens 215 includes microscopic magnification optics designed to provide 60-350× magnification for enhanced inspection. Thus, the numerical aperture NA-2 at the plane of the mask M-2 on the inspector tool is significantly greater than the numerical aperture NA-1 at the plane of mask M-1 of the lithography tool. Thus, each of these optical systems induce different optical effects in the images produced.

An embodiment of the present invention can utilize standard inspection apparatus 200 such as described in simplified schematic representation of FIG. 3. Such an embodiment uses an illumination source 202 that produces light 203 that is directed through illumination optics 210 to produce a light beam 213 that is directed onto and through a portion of the mask M-2.

For example, the illumination source 202 can be a laser or a filtered lamp. In one embodiment, the illumination source 202 is a 193 nm laser. As explained above, the inspection apparatus 200 is configured with a numerical aperture NA-2 at the plane of mask M-2 that is higher than the numerical aperture NA-1 at the plane of mask M-1 of the lithography tool. The mask M-2 to be inspected is placed on a horizontal plane at a specified location and exposed to the illumination source 202. The patterned image from the portion of mask M-2 is directed through the microscopic magnification optical system 215 which projects the patterned image onto an electronic sensor 250.

The sensor 250 collects an image that is transmitted through the mask, or alternatively, or in addition, an additional sensor and associated optics (not shown) may be positioned to collect an image that is reflected by the mask. In one embodiment, the sensor 250 is a sensor array using time delay integration ("TDI") technology, although other types of detectors could be used, including charged coupled device ("CCD") sensors, CCD arrays, TDI sensors, PMTs, and other electronic sensors known to those with skill in the art.

The images captured by the sensor 250 are processed by processing circuitry 260. The processing circuitry 260 may form a part of the inspection apparatus, or alternatively, can be a separate apparatus located remotely from the inspection apparatus. In one embodiment, the processing circuitry 260 includes one or more microprocessors and associated memory embodied in a computer apparatus and configured to enable the principles described herein. For example, the Teron series Reticle Defect Inspection Systems, made by KLA-Tencor Corporation, of San Jose, Calif., are computer-controlled inspection systems that targets 1×nm logic and 2×nm half-pitch memory nodes.

3. Improved Optical Inspection Methods

However, for high-resolution masks, such as NIL or EUV masks, less expensive methods of inspection can be employed by simply evaluating only the test image. For example, in FIG. 3, a first image of a portion of mask M-2 that has only fine patterns that are outside the imaging bandwidth of the inspector is captured by the sensor 250 then processed by the processing circuitry 260. Mask M-2 may have coarser patterns elsewhere that are within the optical bandwidth of the inspector, but such patterns are not relevant here. In this example, this first image of a defect-free portion of the mask will ideally have no visible features since these features are outside of the optical bandwidth of the inspector. However, there may be some features visible in the image due to imperfections in the tool itself. A simple method of processing the first image would be to subject it to a filtering step using knowledge of the imaging optics. The filtering step could be implemented in the signal processing circuitry 260, or by adding physical filter elements to appropriate portions of the imaging optics.

Figure 4A:
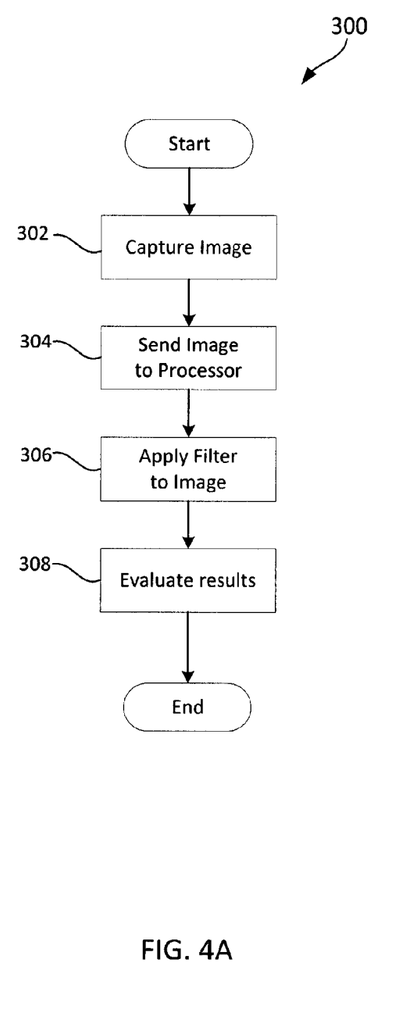
FIG. 4A is a flow chart illustrating a process for capturing and filtering an image that is directed onto a lithographic mask.

Referring to FIG. 4A, a process 300 for operating on the test image with the signal processing circuitry 260 is illustrated. In step 302, a first image having an optical bandwidth consistent with that of the inspection apparatus 200 is captured by the sensor 250. In step 304, the captured image is provided to the signal processing circuitry 260. In step 306, a filtering function is applied to the captured image by the signal processing circuitry 260. The filtering function is intended to remove the undesirable portions of the image, i.e., remnants of the actual pattern, so that only features of interest, such as defects, remain in the resultant image. In step 308, the resultant image is evaluated by the signal processing circuitry 260 to determine if any of the remaining artifacts are, in fact, undesirable defects in the mask. For example, if an EUV mask has lines which are not fully resolved but not completely out of the optical band, and the pitch of the lines is known, a filter can be developed to remove the frequencies associated with the image of the lines, thereby leaving much of the image of any defects.

Figure 4B:
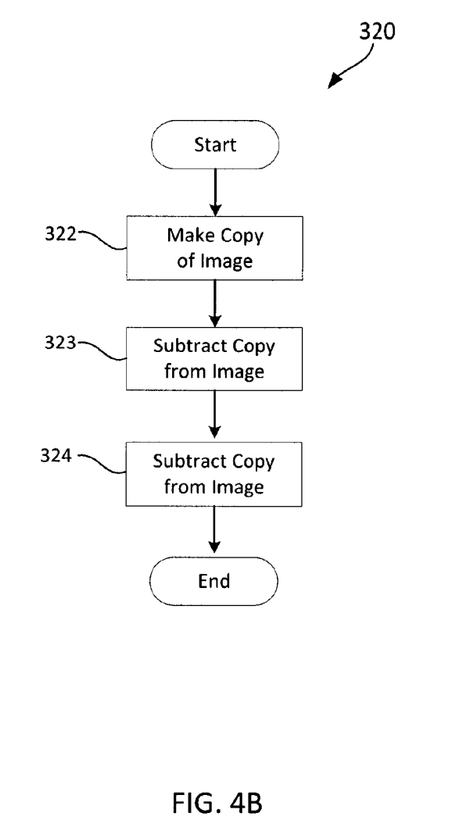
FIG. 4B is a flow chart illustrating an example of a filtering process.

FIG. 4B illustrates one embodiment of a process 320 for implementing a filter in step 306. In step 322, the signal processing circuitry makes a copy of the original image. In step 323, the signal processing circuitry processes the copy so as to retain artifacts due to the processor but to remove possible defects of interest. In step 324, the processed copy is subtracted from the original, and returning to process 300, the result is evaluated in step 308. In the absence of defects, this filter should result in an image that is more uniform with fewer inspector defects. Any remaining features in the resultant image are more likely to reflect defects on the mask, which may or may not be significant. One method of processing the copy of the image is to replace every pixel with the average value of all the pixels in its row before it is subtracted from the original. Alternatively, the processed copy could have the column averages of the copy subtracted from the original. In yet another alternative, the previous two alternatives could be applied serially.

In general, inverse filtering can be applied to the original image to generate a derived or "synthetic" image which enables the processor to remove or otherwise process the original image to thereby evaluate other image artifacts that are not in the original image. Inverse filtering can be accomplished, for example, by taking a Fourier Transform of the image.

Thus, a filter can be applied in the frequency domain to remove the expected portions of the image (i.e., the pattern). After filtering in the frequency domain and transforming back to image space, the remaining artifacts can be evaluated as defects. Alternatively, a filter can be applied in the image domain by convolution. Further, physical filters can be implemented for specific cases, but it is far easier and more flexible to implement a processor control for an adjustable optical system.

Figure 5A:
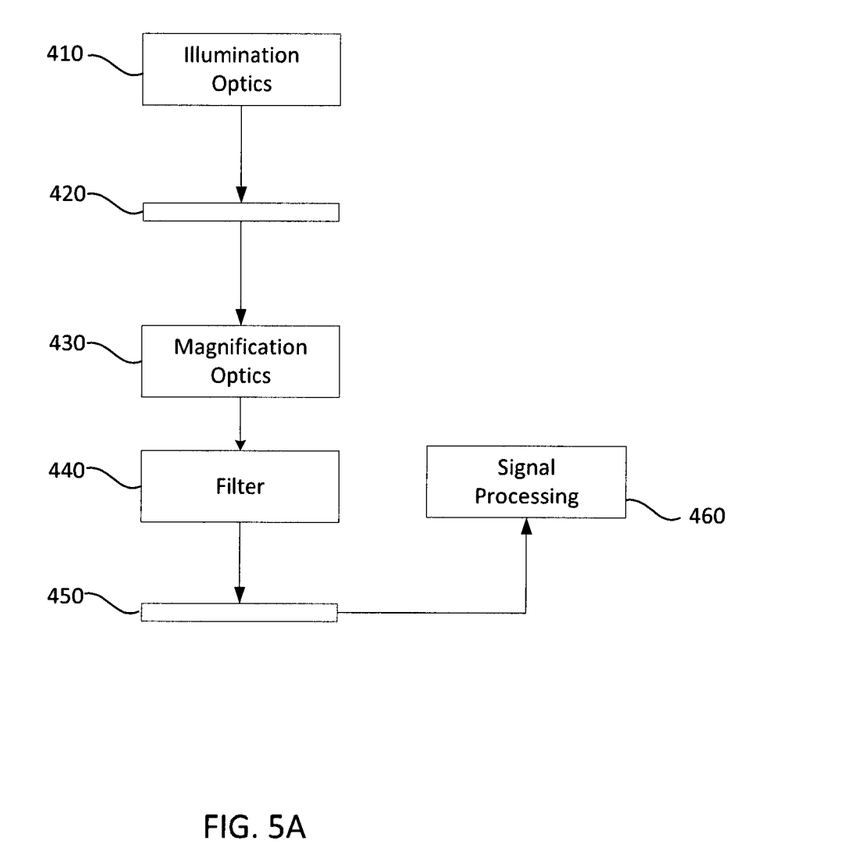
FIG. 5A is a simplified schematic diagram illustrating an arrangement for filtering an image before it is directed onto a lithographic mask.

FIG. 5A illustrates a simplified block diagram of one embodiment of an optical inspection scheme. Illumination optics 410 direct radiation through mask 420 and into magnification optics 430, then through a filter 440, before the radiation is measured by sensor 450. The sensor 450 is coupled to a signal processor 460, which processes and evaluates the signals received from the sensor. The filter 440 can be implemented in various ways as described above, for example, as a specific optical filter, or as a programmable adjustable optical filter. Using this scheme, the image detected by sensor 450 is already filtered to remove the base pattern such that all that remain are artifacts to be evaluated as defects.

Figure 5B:
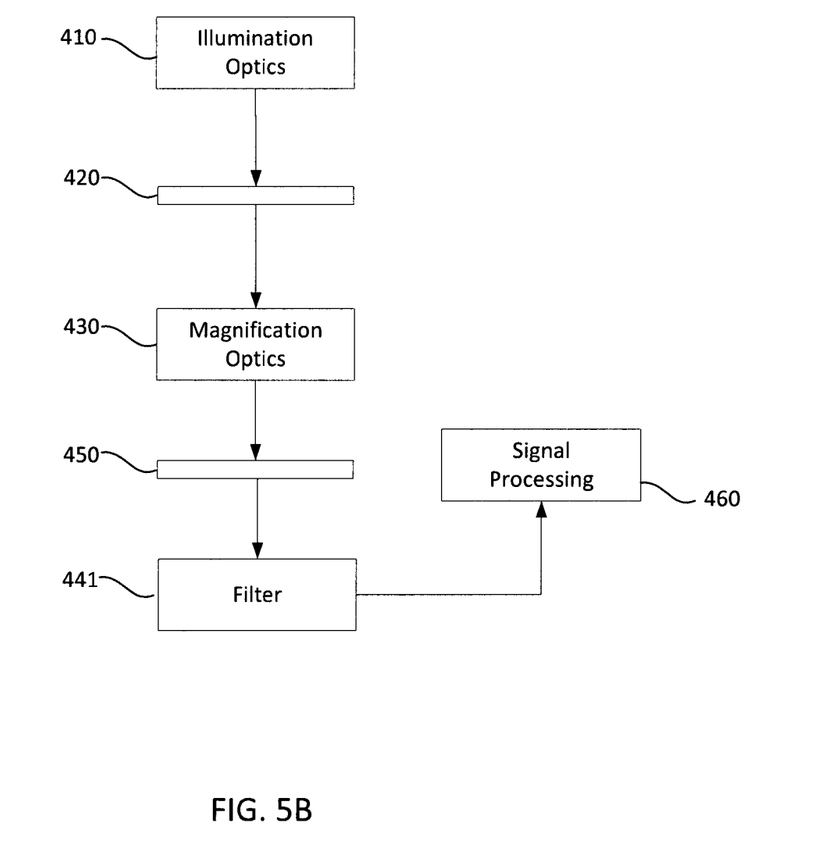
FIG. 5B is a simplified schematic diagram illustrating an arrangement for filtering an image after it is directed onto a lithographic mask.

FIG. 5B illustrates another embodiment, similar to FIG. 5A, except that the filter 441 is located after the sensor rather than before. Using this scheme, the original image is first detected by sensor 450, and then filtered to remove the base pattern such that all that remain are artifacts to be evaluated as defects.

Figure 5C:
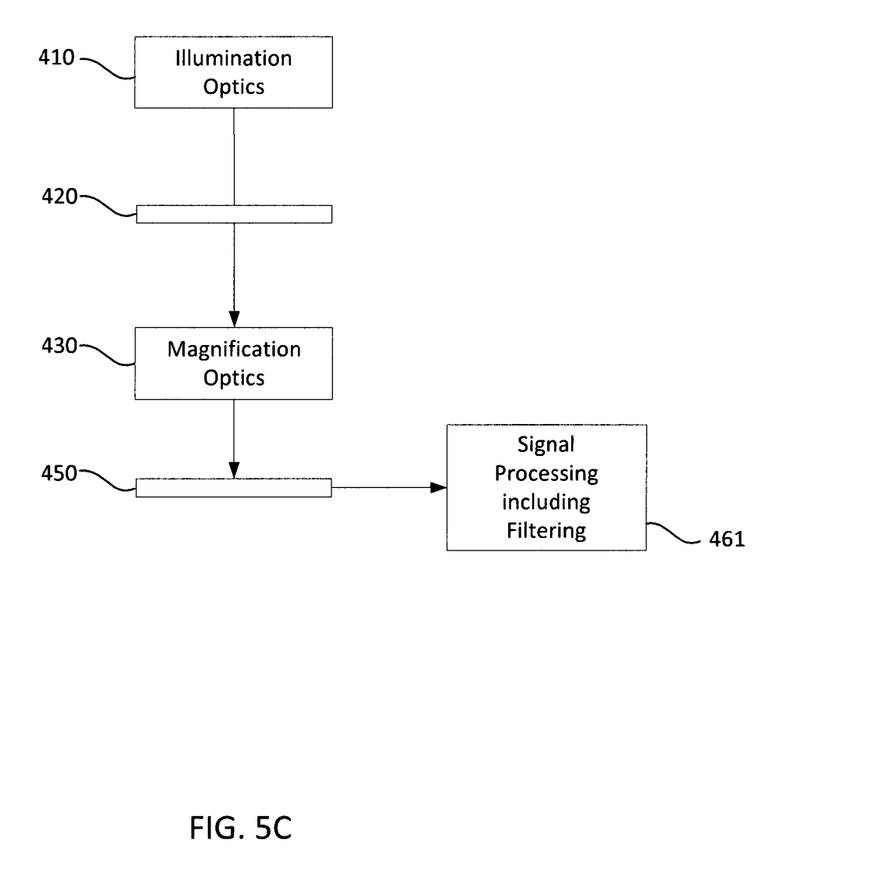
FIG. 5C is a simplified schematic diagram illustrating an arrangement for filtering an image directed onto a lithographic mask using a signal processor.

FIG. 5C illustrates yet another embodiment. In this embodiment, the original image is detected by sensor 450 and provided to the signal processor 461, which can implement any programmed filter specifications to act on the original image, and can be programmed to perform mathematical operations in the frequency domain using the original image and the filtered image to obtain a resultant image in the frequencies of interest.

Figure 5D:
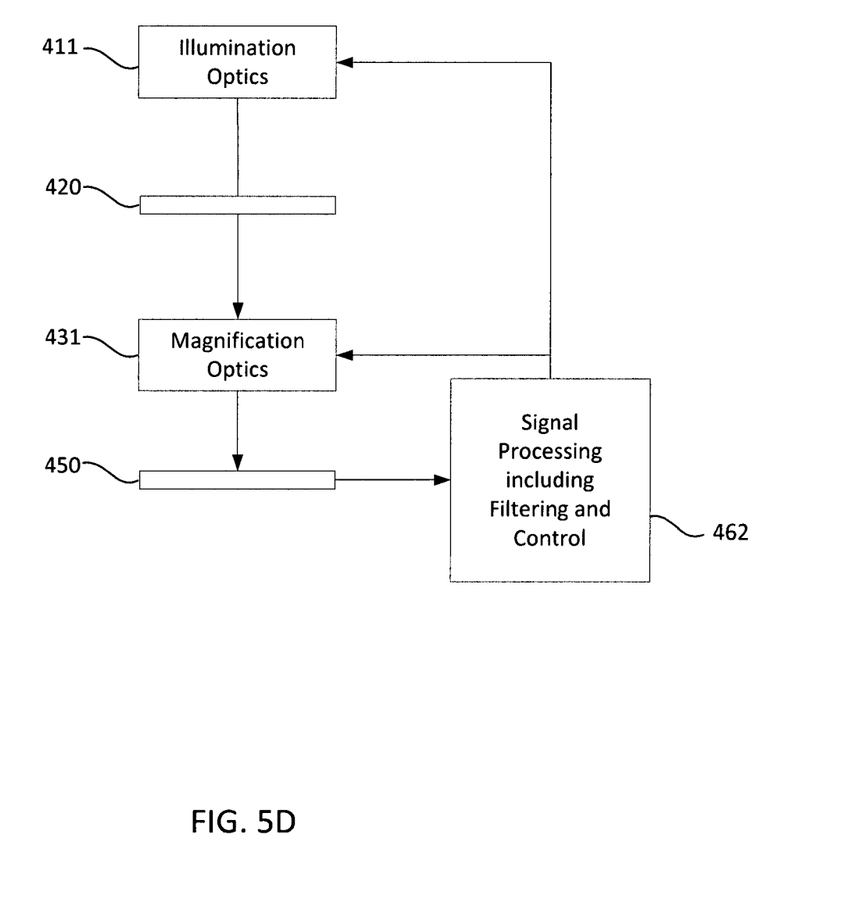
FIG. 5D is a simplified schematic diagram illustrating an arrangement for filtering an image directed onto a lithographic mask using a signal processor and for controlling the illumination optics and magnification optics using the signal processor.

Finally, FIG. 5D illustrates an embodiment in which the original image is detected by sensor 450 and provided to the signal processor 462. In this embodiment, various parameters of the illumination optics 411 are adjustable, for example, the effective bandwidth of the emitted radiation, the coherence of emitted radiation, and the numerical aperture of the illumination optics. Likewise, various parameters of the magnification optics 431 are also adjustable, for example, the numerical aperture. Further, the signal processor 462 can be programmed to implement filter specifications to act on the original image; can also be programmed to perform mathematical operations in the frequency domain using the original image and the filtered image to obtain a resultant image in the frequencies of interest; and further, can be programmed to provide adjustment to the illumination optics 411 and the magnification optics 431 in order to implement a specified signal processing scheme.

As another example, one could design a filter that passes everything that is not the desired image, e.g., as a low pass filter and/or a high pass filter. Such a filtering function would not return the desired image, but would return whatever artifacts existed. The filtered image could then be subtracted from the original image, and the artifacts would be removed, leaving only the desired image.

In some cases, the base pattern of the mask is simply not resolved by the inspection tool, especially in regions that are periodic and have well defined diffraction orders that are outside the numerical aperture of the inspection system, and yet the inspection tool will still be able to detect small defects using optical methods.

In the extreme example of a very small defect which is not periodic, the inspection tool will image the defect with the same size as its fundamental resolution spot, which would be large compared to the desired structures on the mask. In this case, the inspection tool can detect the defect directly on the test image without the added noise or computational cost of subtracting the reference.

In the case described above where one lithography step produces fine, one-dimensional lines which are not fine enough to be outside the optical bandwidth of the inspection tool, the inspection tool can perform subtraction more efficiently if the base pattern is removed, and yet still detect small defects. The inspection tool can perform a variant of cell-to-cell inspection where the cell displacement has a direction parallel to the lines and a magnitude not constrained by mask. In this case, the inspection tool can choose the magnitude of the displacement to minimize spurious noise between the test and reference images, or use multiple references to allow double arbitration, and, if the chosen cell magnitude is not very much larger than defect image, apply a matched filter designed with knowledge of that magnitude.

As is true for in general for both inspection and lithography, some illumination shapes are better than others, and can affect both the signal and the noise. Highly coherent illumination can minimize noise or interference from residual resolution of patterns on the mask. As is well known in the art, reducing coherence broadens the optical pass band, thus enhancing the ability to sense patterns. Further, using highly coherent illumination, inspection of masks with their patterns outside of the optical band is very similar to inspection of blanks for pit and bump defects, a technique that is well known in the art, and many of the methods employed for optimizing blank inspections are applicable here. For example, defects will often appear as phase defects that have greater signal when the system focuses at substantial offset from either the nearer substrate surface or the nearer pattern surface.

Typically, a test image will be of a small portion of the mask and the total area to be inspected. For example, with a square pixel size of 55 nm, a total inspected square of 100 mm, and square inspection portions of 1000 pixels, there will be approximately 3.3 million inspection portions. In embodiments which detect defects on the test image without subtracting a reference image, it can be both convenient and advantageous to subtract a synthetic reference derived from the test image itself. A method well known in the art for detecting phase defects on blank masks is to subtract the column averages from columns of the test image portions and/or the row averages from rows of that image. The synthetic reference could include other estimates of the background. For example, a low-pass linear filtered version of the image could be included in the synthetic reference. Another possibility is equivalent to high-pass filtering the test image portion before detection. Such filtering would be advantageous in at least the situation where all of the base pattern is outside the optical bandwidth of the imaging system, but has spatial variations in the density of the pattern on a scale much larger than the critical dimensions of the pattern but small compared to, for example, the field of view of the imaging system.

Interactions of the nearly or totally invisible base pattern, the illumination shape, the illumination polarization, and the detection analysis can affect the defect signal. Thus, there can be tradeoffs between signal and noise in choosing illumination for the mask and defects of interest. Preferred illuminations would give larger signal-to-noise ratios.

There may be cases where the desired patterns on the mask are nearly outside the optical bandwidth of the imaging system, but not quite. In this case it would be preferred to restrict the numerical aperture of the imaging to reduce noise in the test images by putting the pattern more completely outside the optical bandwidth of the system.

In the situation where the base pattern is outside the optical bandwidth of the inspector, many standard inspection algorithms will simply fail because they cannot align the test and the reference images.

In the situation where there are one-dimensional lines, the noise due to optical aberrations in the systems is substantially reduced by using a time-delay-and-integration-based ("TDI") imaging system. A TDI system, where the scan direction is in the X dimension and the resulting sets of pixels are arrayed in the Y dimension, the noise due to aberrations is lower if the X axis is arranged to be parallel with the lines. Each pixel will average over aberrations as a point scans in Y, resulting in a lower expected aberration. Also each pixel in subtracted images will have an identical aberration effect, since they are at the same Y, which should cancel out in the subtraction. Generic cell-to-cell subtractions would have greater noise due to different local aberrations from one Y location to another.

While one or more implementations have been described by way of example and in terms of the specific embodiments, it is to be understood that one or more implementations are not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

The invention claimed is:

1. A method comprising:
   illuminating a portion of a lithographic mask having a high-resolution mask pattern with an incident light beam having a characteristic optical bandwidth and focused through an optical element;
   capturing light that is transmitted through the mask or reflected by the mask, the captured light forming a sensed image file; and
   using a processor to:

apply a filter function to the sensed image file to obtain a filtered image file having the high-resolution mask pattern removed and having desired frequency characteristics;

perform a mathematical operation in the frequency domain using the sensed image file and the filtered image file to obtain a resultant image in accord with an image processing scheme; and evaluate the resultant image for indications of defects in the lithographic mask.

2. The method of claim 1, wherein the illuminating step includes illuminating the test portion with a coherent incident light beam.

3. The method of claim 2, wherein the coherence of the incident light beam is adjustable, and the processor is used to adjust the coherence.

4. The method of claim 1, wherein the optical element has a numerical aperture, the method further comprising restricting the numerical aperture such that the captured light falls outside the characteristic optical bandwidth of the incident light beam.

5. The method of claim 4, wherein the numerical aperture of the optical element is adjustable, and the processor is used to adjust the numerical aperture.

6. The method of claim 1, wherein the step of capturing light uses time delay and integration based imaging.

7. The method of claim 1, wherein the step of applying a filter function includes applying a Fourier Transform to the sensed image file.

8. The method of claim 1, wherein the step of applying a filter function includes filtering out all images in the sensed image file not having the desired frequency characteristics, and subtracting the filtered sensed image from the sensed image file to form the resultant image.

9. The method of claim 1, wherein the step of capturing light includes scanning the test portion in a lateral dimension relative to a plane of the mask.

10. The method of claim 9, wherein the lateral dimension is arranged to be parallel with linear features formed on the test portion.

11. The method of claim 10, further comprising:
scanning the test portion in the X dimension to return an array of image intensity values in the Y dimension; and
subtracting an average of the image intensity values in the Y dimension from the sensed image to form a resultant image.

12. A method, comprising:
illuminating a portion of a lithographic mask having a high-resolution mask pattern with an incident light beam having a characteristic optical bandwidth and focused through an optical element having a characteristic numerical aperture;
optically filtering light that is transmitted through the mask or reflected by the mask to obtain a sensed image having the high-resolution mask pattern removed and having desired frequency characteristics;
capturing the sensed image with a sensor; and
evaluating, using a processor, the sensed image for indications of defects in the lithographic mask.

13. The method of claim 12, wherein the illuminating step is controlled by the processor, the processor configured to adjust the optical bandwidth of the incident light beam and to adjust the numerical aperture of the optical element.

14. The method of claim 13, wherein the illuminating step includes illuminating the portion of the mask with a coherent incident light beam having an adjustable coherence, and the processor is configured to adjust the coherence of the incident light beam.

15. The method of claim 12, wherein the filtering step is controlled by the processor, the processor configured to perform a filtering function on the sensed image to obtain a filtered image having desired frequency characteristics, and to perform a mathematical operation in the frequency domain using the sensed image and the filtered image to obtain a resultant image in accord with an image processing scheme, and to evaluate the resultant image for indications of defects.

16. The method of claim 12, wherein the step of filtering includes filtering out all images in the sensed image not having the desired frequency characteristics, and subtracting the filtered sensed image from the sensed image to form a resultant image, wherein the processor evaluates the resultant image for indications of defects.

17. An optical inspection apparatus comprising:
a stage for holding a lithographic mask having a high-resolution mask pattern;
a light source positioned to emit an incident light beam toward the mask along an optical axis, the incident light beam having a characteristic optical bandwidth;
illumination optics having a characteristic numerical aperture and positioned on the optical axis between the light source and the mask to focus the incident light beam onto a portion of the mask;
a sensor positioned to capture light that is transmitted through the mask or reflected by the mask, the captured light forming a sensed image;
an optical filter coupled to receive the sensed image and generate a filtered image having the high-resolution mask pattern removed and having desired frequency characteristics; and
a processor programmed with instructions to evaluate the filtered image for indications of defects in the lithographic mask.

18. The optical inspection apparatus of claim 17, wherein the processor is programmed with instructions to adjust the optical bandwidth of the incident light beam and to adjust the numerical aperture of the optical element.

19. The optical inspection apparatus of claim 18, wherein the light source emits a coherent incident light beam having an adjustable coherence, and the processor is programmed with instructions to adjust the coherence of the incident light beam.

20. The optical inspection apparatus of claim 17, wherein the optical filter filters out all images in the sensed image not having the desired frequency characteristics, and the processing element subtracts the filtered sensed image from the sensed image to form the filtered image.

* * * * *